(12) United States Patent
Koch et al.

(10) Patent No.: US 8,455,641 B2
(45) Date of Patent: Jun. 4, 2013

(54) METHOD FOR PRODUCING 4,4'-(PROPANE-1,2-DIYL)-DIPIPERAZINE-2,6-DIONE

(75) Inventors: Andreas Koch, Linz (AT); Erwin Neufellner, Linz (AT)

(73) Assignee: Cyathus Exquirere Pharmaforschungs GmbH, Vienna (AT)

( * ) Notice: Subject to any disclaimer, the term of this patent is extended or adjusted under 35 U.S.C. 154(b) by 54 days.

(21) Appl. No.: 12/516,348

(22) PCT Filed: Nov. 23, 2007

(86) PCT No.: PCT/AT2007/000529
§ 371 (c)(1),
(2), (4) Date: Jan. 18, 2010

(87) PCT Pub. No.: WO2008/061270
PCT Pub. Date: May 29, 2008

(65) Prior Publication Data
US 2010/0152447 A1  Jun. 17, 2010

(30) Foreign Application Priority Data
Nov. 24, 2006  (AT) ................................ A 1958/2006

(51) Int. Cl.
*C07D 241/04* (2006.01)
(52) U.S. Cl.
USPC ...................................................... 544/385
(58) Field of Classification Search
USPC ...................................................... 544/385
See application file for complete search history.

(56) References Cited

U.S. PATENT DOCUMENTS

| | | | |
|---|---|---|---|
| 2,428,353 A | 10/1947 | Bersworth | |
| 3,196,153 A | 7/1965 | Joachim | |
| 3,941,790 A | 3/1976 | Creighton | |
| 5,618,936 A * | 4/1997 | MacDonald et al. | 544/357 |

FOREIGN PATENT DOCUMENTS

| | | |
|---|---|---|
| EP | 0 330 381 | 8/1989 |
| GB | 961 065 | 6/1964 |
| WO | WO 2007/053415 | * 5/2007 |

OTHER PUBLICATIONS

Herman, et al. Research Communications in Chemical Pathology and Pharmacology, 48(1), 1985, 39-55.*
Wikipedia, http://en.wikipedia.org/wiki/Fischer-Speier_esterification, accessed Sep. 20, 2011.*
Organic Chemistry Portal, http://www.organic-chemistry.org/namedreactions/fischer-esterification.shtm, accessed Sep. 20, 2011.*
D.T. Witiak et al., "Study of trans-cyclopropylbis (diketopiperazine) and chelating agents related to ICRF 159, Cytotoxicity, mutagenicity, and effects on scheduled and unscheduled DNA synthesis", Journal of Medicinal Chemistry, vol. 20, No. 5, pp. 630-635, May 1977.
E.H. Herman et al., "Comparison of the Protective Effect of ICRF-187 and Structurally Related Analogues against Acute Daunorubicin Toxicity in Syrian Golden Hamsters", Research Communications in Chemical Pathology and Pharmacology, PJD Publications Ltd., vol. 48, No. 1, pp. 39-55, Apr. 1, 1985.

* cited by examiner

*Primary Examiner* — Douglas M Willis
(74) *Attorney, Agent, or Firm* — Cozen O'Connor

(57) ABSTRACT

A method for preparing compounds of the formula (I) by the cyclization of tetraacetic acid alkyl esters of the formula (II) in the presence of ammonia and formamide as well as to the compounds of the formula (II), which are used in this method.

$$HN\underset{C(O)-CH_2}{\overset{C(O)-CH_2}{\diagdown}}N-CH(CH_3)-CH_2-N\underset{CH_2-C(O)}{\overset{CH_2-C(O)}{\diagup}}NH \quad (I)$$

6 Claims, No Drawings

METHOD FOR PRODUCING 4,4'-(PROPANE-1,2-DIYL)-DIPIPERAZINE-2,6-DIONE

RELATED APPLICATION

This is a U.S. national stage of application No. PCT/AT2007/000529, filed on Nov. 23, 2007.

This application claims the priority of Austrian Patent application no. 1958/2006, filed Nov. 24, 2006, the entire subject matter of which is hereby incorporated by reference.

FIELD OF THE INVENTION

This invention relates to a new method for preparing 4,4'-(1-methyl-1,2-ethandiyl)-bis-(2,6-piperazinedione). More specifically this invention relates to a new method for preparing 4,4'-(1-methyl-1,2-ethandiyl)-bis-(2,6-piperazinedione) in improved quality and yield. Moreover this invention relates to new intermediate compounds employed in this method.

BACKGROUND OF THE INVENTION 4,4'-(1-methyl-1,2-ethandiyl)-bis-(2,6-piperazinedione) has the general formula (I)

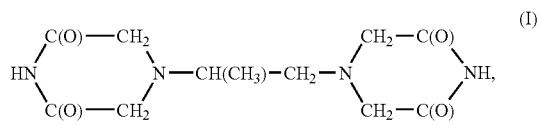

The compound of the formula (I) may be present in the form of two enantiomers as (S)-(+)-4,4'-(1-methyl-1,2-ethandiyl)-bis-(2,6-piperazinedione), also referred to as Dexrazoxan, and as (R)-(−)-4,4'-(1-methyl-1,2-ethandiyl)-bis-(2,6-piperazinedione), also referred to as Levorazoxan, as well as in the form of a racemate, (S,R)-4,4'-(1-methyl-1,2-ethandiyl)-bis(2,6-piperazinedione), also referred to as Razoxan. In conjunction with this invention a "compound of the formula (I)" or "4,4'-(1-methyl-1,2-ethandiyl)-bis-(2,6-p-piperazinedione)", respectively, refers to the S-enantiomer, the R-enantiomer as well as to the racemate.

Regardless of its stereochemistry the compound of the formula (I) has an antitumor effect. In the past, the S-enantiomer of the compound of the formula (I), Dexrazoxan, which is known to be effective against tumors and other forms of cancer and which is also useful as a synergist in combination with other anticancer agents, has achieved special relevance. Particularly with regard to sarcoma, lymphosarcoma and leukaemia, it has been found that Dexrazoxan shows an activity and is particularly effective when used in a regime together with Adriamycin.

In the prior art several preparation methods for the compound of the formula (I) have been known for a long time. For example, in the U.S. Pat. No. 3,941,790 and No. 4,275,063, to Creighton, three methods for preparing bisdiketopiperazines, wherein the compounds of the formula (I) are also included, are described. In the first method, (S)-1,2-diaminopropane is reacted with chloroacetic acid to form (S)-1,2-diaminopropane-tetraacetic acid. Subsequently tetraacetic acid is reacted with formamide under nitrogen at an elevated temperature to the corresponding compound of the formula (I). In the second method tetraacetic acid is prepared as previously described, transferred to the corresponding tetraacetic acid amide by reacting with ammonia and the latter subsequently cyclizised to polyphosphorous acid or phenol by heating. This method is said to be particularly beneficial, when the tetraacetic acid tends to decarboxylate during heating. As a third method, reacting of a tetranitrile with sodium amide in formamide and the subsequent treating of the resulting product with hydrogen chloride in methanol are mentioned. According to Creighton this alternative method has the benefit to be a low-temperature technique. All these methods are stereoselective methods, i.e. therefore the employed intermediate compounds in the form of tetraacetic acid, tetraamide or tetranitrile should already be available in the stereochemical configuration desired for the compound of the formula (I).

The intermediate compounds employed in the aforementioned methods, such as tetraacetic acid, may be prepared in different ways. Beside the already aforementioned preparation methods, for example, in British Patent No. 978.724, J.R., to Geigy A G, a method for forming tetraacetic acid is described, wherein diamines are reacted with formaldehyde and hydrogen cyanide to form a tetranitrile, which is saponified. In U.S. Pat. No. 2,461,519, Bersworth et al., they teach a method for preparing 1,2-diaminopropane-tetracarboxylic acid by reacting 1,2-diaminopropane with formaldehyde and sodium cyanide at an alkaline pH-value.

A main problem with the preparation of the compound of the formula (I) is generally the purification of the intermediate compounds, which is costly and difficult to achieve on a commercial scale. With numerous methods, for example, intermediate compounds, such as tetraacetic acid, are obtained together with high amounts of alkali metal salts as a by-product, which prior to cyclization to the compound of the formula (I) have to be separated.

These problems of the aforementioned preparation methods are particularly based on the fact that the employed tetraacetic acid like the tetraamides, the tetranitriles and the compound of the formula (I) themselves are very polar hydrophilic substances and form salts with the strong bases, as being required in the preparation method. Consequently, this always results in difficulties in the required separation of the non-reacted precursor compounds and the resulting by-products.

The problems arising with and through the purification of the precursor compound in known preparation methods are described in detail in International Patent Application No. 93/08172, to P. L. MacDonald. Thus, to solve these problems, a method for preparing the compound of the formula (I), to be precisely, Deraxozan, is suggested, wherein the latter shall be obtained in high yields without, prior to cyclization to Dexrazoxan, performing a purification of the intermediate tetraacetic acid compound. However, by this method Dexrazoxan is obtained together with higher amounts of salt-by-products, which results in difficulties in the production of salt-free Dexrazoxan.

Beside methods for preparing compounds of the formula (I) or analoguous compounds thereof, wherein tetraacetic acid, tetraamide or tetranitrile are employed as a intermediate product, a method for preparing cis- and trans-cyclopropyl-bis-2,6-(piperazinedione), two compounds which are analoguous to the compound of the formula (I), is also described in the literature, which method processes via the corresponding tetraacetic acid methyl ester as a precursor compound. D. T. Witiak et al, Journal of Medicinal Chemistry, Bd. 20, Nr. 5, pp 630-635 (1977), and Journal of Medicinal Chemistry, Vol. 21, No. 12, pp 1194-1197 (1978), describe the cyclization of the corresponding tetraacetic acid methyl ester in the form of the hydrochloride with an excess of ammonia and sodium methoxide in methanol for preparing the trans-compound. The yield of the desired trans-compound is poor and amounts to only 27% prior to purification. According to the authors, the application of this method for preparing the corresponding cis-compound was not successful: For the preparation of the cis-compound, the tetraacetic acid methyl ester is cyclisised with sodium hydride and formamide in DME. The yield of the trans-compound is quoted with 36.5%.

Witiak et al. suggest tetraacetic acid methyl ester exclusively for the preparation of the aforementioned compounds. There is no evidence in it to employ tetraacetic acid methyl ester compounds as precursor compounds for the preparation of analoguous compounds. Rather, the problems in preparating cis- and trans-isomers of the desired compound suggest that the employment of such compounds as a precursor compound is not readily possible.

SUMMARY OF THE INVENTION

The invention relates to a method for preparing a compound of formula (I)

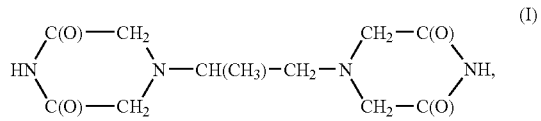

wherein the method comprises cyclizing a tetraester of the formula (II) $(ROOCCH_2)_2N-CHCH_3-CH_2-N(CH_2COOR)_2$, wherein R stands for alkyl, with ammonia in formamide.

One object of the present invention is to provide a method for preparing the compound of the formula (I), which enables the preparation of this compound in good yield, also on a commercial scale and overcomes the problems of the technique-known methods.

This and other objects are attained in accordance with one aspect of the present invention directed to a method which comprises the step of cyclizating a 1,2-diaminopropane-N,N,N',N'-tetraacetic acid alkyl ester (hereinafter referred to as "tetraacetic acid alkyl ester") with ammonia in formamide, wherein "alkyl" herein preferably stands for $(C_1-C_3)$-alkyl, and comprises both "$C_3$-alkyl" n-propyl, isopropyl, as well as cyclopropyl.

DETAILED DESCRIPTION OF THE INVENTION

The method according to an embodiment of the invention is based on the observation of the surprising characteristics of the alkyl esters of tetraacetic acid, such as a reduced polarity and hydrophility compared to the known intermediate compounds, which is used to provide an improved method for preparing the compound of the formula (I). Moreover, due to the higher reactivity of these esters, the ring closure to the compound of the formula (I) may be achieved under simpler conditions with regard to both the number of required reaction steps and measures as well as the reaction conditions required therefore.

Further advantages of methods according to the invention are the application of ammonia and formamide, two common chemicals, wherein, in a method according to an embodiment of the invention, formamide is also employed as a solvent. Methanol, resulting during cyclization can be removed from the reaction mixture by simple distillation. Further details with respect to a method according to the invention and a preferred embodiment may also be learned from the following examples.

The invention also relates to the tetraacetic acid alkyl esters employed in the method according to the invention, having the formula (II)

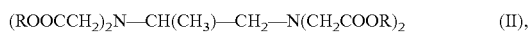

wherein R stands for alkyl. Preferably R is a $(C_1-C_3)$-alkyl such as methyl, ethyl or propyl.

The compounds of the formula (II), which are valuable precursor compounds for the compounds of the formula (I), are novel compounds except for the tetraacetic acid methyl ester, which is described by E. H. Herman et al. in Research Communications in Chemical Pathology and Pharmacology, Vol. 48, No. 1, pp 39-55 (1985). The tetraacetic acid alkyl ester may be prepared using technique-known methods, also as described in the following examples.

A preferred method in conjunction with an embodiment of the present invention for preparing the tetraacetic acid alkyl ester of the present invention comprises reacting a diamine of the formula (III)

$$H_2N-CH(CH_3)-CH_2-NH_2 \quad (III)$$

or a suitable salt thereof with chloroacetic acid and the subsequent treatment with alkyl alcohol to form the tetraacetic acid alkyl esters of the formula (II):

wherein R stands for alkyl, preferably $(C_1-C_3)$-alkyl, such as methyl, ethyl, or propyl.

The thus obtained tetraacetic acid alkyl esters are subjected to a further cyclization step in the presence of ammonia and formamide in order to obtain the compound of the formula (I).

Prior to cyclization to the compound of the formula (I), the tetraacetic acid alkyl esters of the formula (II) may be subjected to a purification, if desired, for example by subjecting them to a distribution between a water immiscible solvent and water to separate the formed alkali metal salts. Particularly ethyl acetate and isopropyl acetate are used as water immiscible solvents.

However, the tetraacetic acid alkyl esters of the formula (II) may be cyclizised to the compound of the formula (I) also without prior purification. This variant of the method represents a particularly preferred embodiment of the method for preparing the compound of the formula (I).

In the particular embodiment of the method according to the invention, higher yields of the compound of the formula (I) as compared to known methods and a sufficient purification of the compound of the formula (I) may be achieved as well. Additionally, further purification and isolation of the tetraacetic acid alkyl esters, which are employed as a precursor compound, is not required.

In the method according to an embodiment of the invention, like in the preferred embodiment thereof, a possible breakdown of the compound of the formula (I) by hydrolysis in the course of the method is minimized. The separation of ionic materials (like the alkali metal salts) may be completely and easily performed by distribution of the tetraacetic acid alkyl esters of the formula (II) between a water immiscible solvent, such as ethyl acetate, isopropyl acetate, and water.

The method according to an embodiment of the invention as well as the preferred embodiment thereof are stereoselective methods, i.e. the precursor compound must be available in the configuration desired for the compound of the formula (I).

Further aspects of the present invention can be learned from the following examples, which are given for illustration purposes and not to limit the invention. Those skilled in the art should appreciate that the details of the method, which are described in the following examples, may be modified within the scope of the present invention. For example, according to the method of the example 5, which has been described for the S-enantiomer, Dexrazoxan, the R-enantiomer, Levorazoxan, and the racemate may be prepared as well. Unless otherwise noted or may be concluded from the context, the percentages relate to weight.

EXAMPLES

Example 1

Preparation of (S)-(+)-1,2-diaminopropane-N,N,N', N'-tetraacetic acid 150.0 g (1.02 Mol) of (S)-(−)-1,2-diaminopropane dihydrochloride are introduced into 780.0 g of deionized water at RT, 578.4 g (6.12 Mol) of chloroacetic acid are added and 1785.0 g (14.28 Mol) of sodium hydroxide 32 percent by weight is proportioned to this solution for 45 min under cooling (at 15° C.). After the addition is completed the reaction mixture is heated to 40° C., wherein starting from 40° C., the reaction is kept exothermal and the temperature is kept under cooling at 40-45° C. After decay of the exothermal reaction stirring for 90 h at 40-45° C. is performed. The alkaline, colourless and clear liquid is narrowed down under vacuum at a bath temperature of 70° C. by approx. the 2.5-fold. The oily crystal slurry is mixed with 1.2 l of methanol, cooled down to 20° C., the salts are filtered off and the residue in the filter is washed with 2×300 ml of methanol. The unified methanolic solutions are completely evaporated in vacuum at a bath temperature of 70° C.

The high-viscosity distillation residue is mixed with 300 ml of deionized water at 70° C. and cooled down to 0° C. Under cooling the pH-value is adjusted to 1,5 by adding 343.8 g of 95% sulphuric acid and after a post-reaction period the thick crystal slurry is mixed with 900 ml of deionized water.

The crystal slurry is stirred over night at 0° C. with 2 l of acetone. The crystals are filtered off and washed with 2×250 ml of a mixture of water/acetone at a ratio of 1:2 and with 2×500 ml of pure acetone.

The unified organic solution is completely evaporated under vacuum at a bath temperature of 70° C., the remaining viscous residue is mixed with a total of 600 ml glacial acetic acid and by adding 5 l of acetone at room temperature the product is precipitated. The suspension is cooled to 5° C., the product is filtered off, washed with 550 ml glacial acetic acid/acetone at a ratio of 1:10 and 2×500 ml acetone and dried at 20° C. under vacuum.

Yield: 272.1 g

Example 2

Preparation of (S)-(+)-1,2-diaminopropane-N,N,N', N'-tetraacetic acid methyl ester The esterification is performed with the isolated (S)-(+)-1, 2-diaminopropane-N,N,N',N'-tetraacetic acid as follows:

37.5 g of (S)-(+)-1,2-diaminopropane-N,N,N',N'-tetraacetic acid together with 756 ml of methanol and 22.5 g of 95% sulfuric acid are heated under reflux for 20 h. The chilled solution is neutralized with a total of 41.5 g sodium hydrogen carbonate and distilled to dryness under vacuum. The remaining residue is distributed between 300 ml of deionized water and 300 ml tert-butylmethylether, and the aqueous phase is extracted with 2×150 ml tert-butylmethylether. The unified organic phases are dried with sodium sulfate, filtered off, and the solvent is evaporated to dryness under vacuum (crude yield: 20.7 g).

The crude product is dissolved in 300 ml of a mixture of tert-butylmethylether/petroleum ether 60/95 at a ratio of 1:2, stirred with 45 g of silica gel 0.06-0.2 mm for 30 min and filtered off. The residue is washed with 2×50 ml of the aforementioned solvent-mixture and the filtrate is evaporated to dryness under vacuum.

Yield: 6.9 g of colourless oil (methyl ester)

Analysis Data:

| Elementary analysis: | | C | H | N | O |
|---|---|---|---|---|---|
| $C_{15}H_{26}N_2O_8$ | calc: | 49.72 | 7.23 | 7.73 | 35.32 |
| | found: | 49.84 | 7.39 | 7.47 | |

Amount of rotation $[\alpha]_D^{20}$ (c=4; methanol): +3.1°

1H-NMR: 0.97 (d, 3H; —CH—CH$_3$); 2.49 (1H; N—CH—CH$_2$—); 2.83 (dd, 2H; N—CH—CH$_2$—); 3.5 (s, 4H; N—CH$_2$—CO); 3.55 (s, 4H; N—CH$_2$—CO); 3.61 (s, 12H; COO—CH$_3$)

13C-NMR: 15.0 (q; —CH—CH$_3$); 51.22 (q; O—CH$_3$); 51.38 (q; O—CH$_3$); 52.07 (t; N—CH$_2$—); 54.99 (t; N—CH$_2$—); 55.96 (d; N—CH—); 58.08 (t; CH—CH$_2$—N); 171.69 (s; —CO—); 172.31 (s; —CO—)

Example 3a

Preparation of (S)-(+)-1,2-diaminopropane-N,N,N', N'-tetraacetic acid ethyl ester The esterification is performed with the isolated (S)-(+)-1, 2-diaminopropane-N,N,N',N'-tetraacetic acid as follows:

25.0 g of (S)-(+)-1,2-diaminopropane-N,N,N',N'-tetraacetic acid together with 725 ml of ethanol and 15.0 g of 95% sulfuric acid are heated under reflux for 120 h. The chilled solution is neutralized with a total of 27.5 g sodium hydrogen carbonate and evaporated to dryness under vacuum. The remaining residue is distributed between 200 ml of deionized water and 200 ml tert-butylmethylether, and the aqueous phase is extracted with 2×100 ml tert-butylmethylether. The unified organic phases are dried with sodium sulfate, filtered off, and the solvent is evaporated to dryness under vacuum (crude yield: 19.7 g).

The crude product is dissolved in 300 ml of petroleum ether 60/95, stirred with 40 g of silica gel 0.06-0.2 mm for 30 min, filtered off, the residue is washed with 2×50 ml of solvent and the filtrate is evaporated to dryness under vacuum.

Yield: 7.1 g of colourless oil (ethyl ester)

Analysis Data:

| Elementary analysis: | | C | H | N | O |
|---|---|---|---|---|---|
| $C_{19}H_{34}N_2O_8$ | calc: | 54.53 | 8.19 | 6.69 | 30.58 |
| | found: | 54.51 | 8.36 | 6.56 | |

Amount of rotation $[\alpha]_D^{20}$ (c=4; methanol): +1.1°

1H-NMR: 1.08 (d, 3H; —CH—CH$_3$); 1.15-1.35 (dd, 12H; —CH$_2$—CH$_3$); 2.5 (m, 1H, N—CH—CH$_2$—); 2.85-3.15 (m, 2H; N—CH—CH$_2$—); 3.5 (s, 4H; N—CH$_2$—CO); 3.6 (s, 4H; N—CH$_2$—CO); 4.0-4.3 (m, 8H; COO—CH$_2$—CH$_3$)

13C-NMR: 13.96 (q; —CH$_2$—CH$_3$); 14.0 (q; —CH$_2$—CH$_3$); 15.12 (q; —CH—CH$_3$); 52.27 (t; N—CH$_2$—CO);

55.28 (t; N—CH$_2$—CO); 56.0 (d; N—CH—CH$_2$—); 58.2 (t; CH—CH$_2$—N); 60.08; 60.15 2×(t; COO—CH$_2$—); 171.22 (s; CO); 171.87 (s; CO)

Example 3b

Preferred

Preparation of (S)-(+)-1,2-diaminopropane-N,N,N', N'-tetraacetic acid ethyl ester 50 g of (S)-(−)-diaminopropane dihydrochloride and 192.8 g of chloroacetic acid in 321 ml of water are treated with 190.4 g sodium hydroxide in 343 ml of water and treated for 132 h at 45° C. The water is evaporated and the resulting thick suspension is mixed with 100 ml ethanol and again completely evaporated. The residue is taken up in 900 ml of ethanol, treated with 90 ml of concentrated sulfuric acid and refluxed for 46 h. The reaction mixture is cooled down to ambient temperature and the acid is neutralized by adding 240 g of sodium carbonate. The precipitate is filtered off, rewashed with 150 ml of ethanol, the filtrate is evaporated and the oily residue is suspended in 250 ml of toluene. Subsequent to sufficient extraction with 2 N hydrochloric acid the aqueous phase is neutralized with solid sodium carbonate (approx. 75 g) and extracted with about 375 ml of toluene. The complete evaporation of the solvents provides 134 g of the ethyl ester as a slight yellow oil. One analytical sample was obtained by column chromatographic purification over silica gel.
Analysis Data:

| Elementary analysis: | | C | H | N | O |
|---|---|---|---|---|---|
| C$_{19}$H$_{34}$N$_2$O$_8$ | calc: | 54.53 | 8.19 | 6.69 | 30.58 |
| | found: | 54.18 | 8.36 | 6.59 | |

Amount of rotation $[\alpha]_D^{20}$ (c=10; methanol): +8.6°
1H-NMR: 1.02 (d, 3H; —CH—CH$_3$); 1.21-1.27 (dd, 12H; —CH$_2$—CH$_3$); 2.5 (m, 1H, N—CH—CH$_2$—); 2.85-3.07 (m, 2H; N—CH—CH$_2$—); 3.5 (s, 4H; N—CH$_2$—CO); 3.6 (s, 4H; N—CH$_2$—CO); 4.05-4.15 (m, 8H; COO—CH$_2$—CH$_3$)
13C-NMR: 14.27 (q; —CH$_2$—CH$_3$); 14.30 (q; —CH$_2$—CH$_3$); 15.41 (q; —CH—CH$_3$); 52.77 (t; N—CH$_2$—CO); 55.60 (t; N—CH$_2$—CO); 56.31 (d; N—CH—CH$_2$—); 58.51 (t; CH—CH$_2$—N); 60.44; 60.52 2×(t; COO—CH$_2$—); 171.56 (s; CO); 172.22 (s; CO)

Example 4a

Preparation of (S)-(−)-1,2-diaminopropane-N,N,N', N'-tetraacetic acid isopropyl ester The esterification is performed with the isolated (S)-(+)-1,2-diaminopropane-N,N,N',N'-tetraacetic acid as follows:
25.0 g of (S)-(+)-1,2-diaminopropane-N,N,N',N'-tetraacetic acid together with 950 ml of isopropanol and 15.0 g of 95% sulfuric acid are heated under reflux for 162 h. The chilled solution is neutralized with a total of 27.5 g sodium hydrogen carbonate and evaporated to dryness under vacuum. The remaining residue is distributed between 200 ml of deionized water and 200 ml tert-butylmethylether, and the aqueous phase is extracted with 1×100 ml tert-butylmethylether. The unified organic phases are dried with sodium sulfate, filtered off, and the solvent is evaporated to dryness under vacuum (crude yield: 21.2 g).

The crude product is dissolved in 300 ml of petroleum ether 40/65, stirred with 40 g of silica gel 0.06-0.2 mm for 30 min, filtered off, the residue is washed with 2×50 ml of solvent and the filtrate is evaporated to dryness under vacuum.
Yield: 10.8 g of slight yellow oil (isopropyl ester)
Analysis Data:

| Elementary analysis: | | C | H | N | O |
|---|---|---|---|---|---|
| C$_{23}$H$_{42}$N$_2$O$_8$ | calc: | 58.21 | 8.92 | 5.90 | 26.97 |
| | found: | 58.12 | 9.08 | 5.70 | |

Amount of rotation $[\alpha]_D^{20}$ (c=4; methanol): −2.6°
1H-NMR: 1.05 (d, 3H; —CH—CH$_3$); 1.15-1.35 (dd, 24H; iPr-CH—(CH$_3$)$_2$); 2.5 (m, 1H, N—CH—CH$_2$—); 2.85-3.15 (m, 2H; N—CH—CH$_2$—); 3.5 (2s, 2×4H; N—CH$_2$—CO); 5.0 (2q, 4H; iPr-CH—(CH$_3$)$_2$).
13C-NMR: 15.44 (q; —CH$_2$—CH$_3$); 21.79 (q; —CH—(CH$_3$)$_2$); 21.85 (q; —CH—(CH$_3$)$_2$); 52.72 (t; N—CH$_2$—CO); 55.88 (t; N—CH$_2$—CO); 56.25 (d; N—CH—CH$_2$—); 58.53 (t; CH—CH$_2$—N); 67.77; 67.79 2×(t; COO—CH—); 170.99 (s; CO); 171.67 (s; CO).

Example 4b

Preferred

Preparation of (S)-(+)-1,2-diaminopropane-N,N,N', N'-tetraacetic acid isopropyl ester 50 g of (S)-(−)-diaminopropane dihydrochloride and 192.8 g of chloroacetic acid in 321 ml of water are treated with 190.4 g sodium hydroxide in 343 ml of water and treated for 114 h at 45° C. The water is evaporated and the resulting thick suspension is refluxed with a mixture of 90 ml concentrated sulphuric acid in 1500 ml of 2-propanol for 41 h. The reaction mixture is cooled down to ambient temperature and the acid is neutralized by adding 240 g of sodium hydrogen carbonate. The precipitate is filtered off, rewashed with 150 ml of 2-propanol, the filtrate is evaporated and the oily residue is suspended in 250 ml of toluene. Subsequent to sufficient extraction with 2 N hydrochloric acid, the aqueous phase is neutralized with solid sodium carbonate (approx. 75 g) and extracted with about 375 ml of toluene. The complete evaporation of the solvents provides 41 g of the isopropyl ester as a slight yellow oil. An analytical sample was obtained by repeating the extractive preparation and subsequent column chromatographic purification over silica gel.
Analysis Data:

| Elementary analysis: | | C | H | N | O |
|---|---|---|---|---|---|
| C$_{23}$H$_{42}$N$_2$O$_8$ | calc: | 58.21 | 8.92 | 5.90 | 26.97 |
| | found: | 58.09 | 9.06 | 5.88 | |

Amount of rotation $[\alpha]_D^{20}$ (c=10; methanol): 0.5°
1H-NMR: 1.05 (d, 3H; —CH—CH$_3$); 1.20-1.22 (dd, 24H; iPr-CH—(CH$_3$)$_2$); 2.49 (m, 1H, N—CH—CH$_2$—); 2.90, 3.04 (m, 2H; N—CH—CH$_2$—); 3.50, 3.53 (2s, 2×4H; N—CH$_2$—CO); 4.99 (2q, 4H; iPr-CH—(CH$_3$)$_2$).
13C-NMR: 15.53 (q; —CH—CH$_3$); 21.92 (q; —CH—(CH$_3$)$_2$); 21.98 (q; —CH—(CH$_3$)$_2$); 52.85 (t; N—CH$_2$—CO); 56.00 (t; N—CH$_2$—CO); 56.36 (d; N—CH—CH$_2$—);

58.63 (t; CH—CH$_2$—N); 67.92; 67.94 2×(t; COO—CH—); 171.10 (s; CO); 171.79 (s; CO).

Example 5

Preparation of (S)-(+)-4,4'-(1-methyl-1,2-ethandiyl)-bis-(2,6-piperazinedione) (Dexrazoxan) (I)

5.1. Preparation of (S)-1,2-diaminopropane-N—N,N,N',N'-tetraacetic acid-tetramethyl ester (II)

10 kg of (S)-(−)-diaminopropane dihydrochloride and 38.5 kg of chloroacetic acid in 65 l water are treated with 38 kg of sodium hydroxide in 69 l water and treated for 70 to 100 h at 45° C. The water is evaporated and the resulting thick suspension is digested with 80 l of methanol, filtrated and the cake is washed with methanol. The filtrate is completely evaporated and the residue is taken up in 180 l methanol, treated with 18 l of concentrated sulfuric acid and refluxed for 6 h. The reaction mixture is cooled down to ambient temperature and the acid is neutralized by adding 20 to 25 kg of sodium hydrogen carbonate. The precipitate is filtered off, the filtrate is evaporated and the oily residue is dissolved in 50 ml of ethyl acetate. Subsequent to sufficient extraction with 2 N hydrochloric acid the aqueous phase is neutralized with solid sodium carbonate and extracted with about 100 l of ethyl acetate. The complete evaporation of the solvents provides about 13.5 kg to 17.3 kg of the desired methyl ester which may be used in the next step without further purification.

5.2. Cyclization to (S)-(+)-4,4'-(1-methyl-1,2-ethandiyl)-bis-(2,6-piperazinedione) (Dexrazoxan) (I)

4.7 kg of gaseous ammonia are added to a solution of 10 kg (S)-(+)-1,2-diaminopropane-N,N,N',N'-tetraacetic acid methyl ester from the aforementioned example in 34 l formamide and the reaction mixture is maintained at 40 to 50° C. under a pressure of max. 5 bar for about 12 h. Thereafter, the reaction mixture is slowly heated to 150° C., obtained methanol is distilled off during heating and the reaction mixture is maintained at 140 to 150° C. for 10 to 12 h. Then the solvent is distilled off, the oily residue is crystallized from methanol to yield 2.9 to 3.7 kg Dexrazoxan, which may be further purified by recrystallization from 1,4-dioxan.

The invention claimed is:

1. A method for preparing a compound of formula (I)

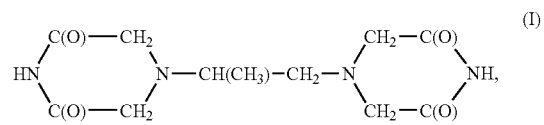

wherein the method comprises cyclizing a tetraester of the formula (II)

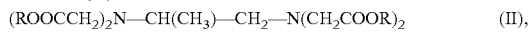

wherein R stands for alkyl, with ammonia in formamide.

2. The method according to claim 1,
wherein R stands for (C$_1$-C$_3$)-alkyl.

3. A method for preparing a compound of formula (I)

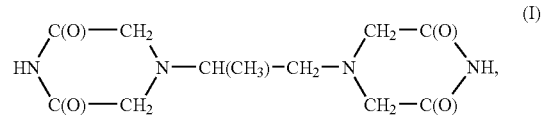

wherein the method comprises:
(a) reacting (S)-1,2-diaminopropane or an acid-addition salt thereof with chloroacetic acid;
(b) treating the product obtained in (a) in an alkyl alcohol with an acid to obtain a compound of formula (II)

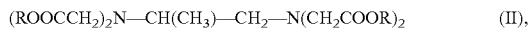

wherein R stands for alkyl, and
(c) cyclizing the compound of formula (II) with ammonia in formamide.

4. The method according to claim 3,
wherein R stands for (C$_1$-C$_3$)-alkyl.

5. The method according to claim 3, wherein the compound of formula (II) is isolated or purified from inorganic salts by distribution between an organic, water immiscible solvent, and water, prior to cyclizing the compound of formula (II) in step (c).

6. The method of claim 3, wherein the acid is a mineral acid.

* * * * *